(12) United States Patent
Hagen et al.

(10) Patent No.: US 8,401,623 B2
(45) Date of Patent: Mar. 19, 2013

(54) DETECTION CHAMBER WITH VARIABLE VOLUME

(75) Inventors: Axel Jakob Hagen, Berlin (DE); Andrea Mueller, Berlin (DE); Axel Kuhn, Berlin (DE); Peter Pawlak, Berlin (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 13/119,616

(22) PCT Filed: Sep. 21, 2009

(86) PCT No.: PCT/IB2009/054129
§ 371 (c)(1),
(2), (4) Date: Mar. 17, 2011

(87) PCT Pub. No.: WO2010/035207
PCT Pub. Date: Apr. 1, 2010

(65) Prior Publication Data
US 2011/0170107 A1    Jul. 14, 2011

(30) Foreign Application Priority Data

Sep. 26, 2008 (EP) .................................. 08165211

(51) Int. Cl.
*A61B 6/00* (2006.01)
(52) U.S. Cl. ....................................... 600/473; 600/476
(58) Field of Classification Search ........... 600/473–480
See application file for complete search history.

(56) References Cited

U.S. PATENT DOCUMENTS

| | | | |
|---|---|---|---|
| 5,596,987 | A | 1/1997 | Chance |
| 5,907,406 | A | 5/1999 | Papaioannou |
| 2004/0092826 | A1 | 5/2004 | Corbeil |

FOREIGN PATENT DOCUMENTS

| | | |
|---|---|---|
| WO | 0056206 A1 | 9/2000 |
| WO | 2008029354 A2 | 3/2008 |
| WO | 2009022300 A1 | 2/2009 |

OTHER PUBLICATIONS

Choe, Regine et al, "Diffuse Optical Tomography of Breast cancer during Neoadjuvant Chemotherapy: A case Study with Comparison to MRI", Medphys Vo, 32, No. 4, 2005, pp. 1128-1139.

*Primary Examiner* — Sanjay Cattungal

(57) ABSTRACT

The invention proposes a detection chamber (5) comprising a fluid-tight measurement volume (20) the size of which can be varied using a movable wall portion (15). Such a detection chamber (5) allows compression of the object to be imaged as well as the use of a matching medium to fill the space inside the measurement volume (20) not filled by the object to be imaged.

18 Claims, 2 Drawing Sheets

DETECTION CHAMBER WITH VARIABLE VOLUME

FIELD OF THE INVENTION

The invention relates to a detection chamber for imaging an object comprising:

a wall structure defining a measurement volume for receiving the object to be imaged, the wall structure being arranged to couple light from a light source into the measurement volume and light emanating from the measurement volume out of the measurement volume;

an opening in the wall structure for accommodating the object to be imaged in the measurement volume;

a movable wall portion, comprised in the wall structure, the movable wall portion being movable as to vary the volume of the measurement volume bounded by the wall structure.

The invention further relates to a device for imaging an object comprising such a detection chamber.

BACKGROUND OF THE INVENTION

In the context of the present application, the term 'object' or 'object to be imaged' covers a turbid medium. A turbid medium is to be understood to mean a substance consisting of a material having a high light scattering coefficient, such as for example an intralipid solution or biological tissue. Further, light is to be understood to mean electromagnetic radiation of a wavelength in the range from 400 nm to 1400 nm. The term "optical properties" covers the reduced scattering coefficient $\mu'_s$ and the absorption coefficient $\mu_a$. Furthermore, "matching optical properties" is to be understood as having a similar reduced scattering coefficient $\mu'_s$ and a similar absorption coefficient $\mu_a$.

In recent years, several methods and devices for examining turbid media, e.g. female breast tissue, have been developed. In particular, new devices for detection and analysis of breast cancer have been developed and existing technologies have been improved. Breast cancer is one of the most occurring types of cancer: in 2002, for example, more than 1.1 million women were diagnosed and over 410.000 women died of breast cancer worldwide. Several types of devices for imaging the interior of a turbid medium by use of light have been developed. Examples for such devices are mammography devices and devices for examining other parts of human or animal bodies. A prominent example for a method for imaging the interior of a turbid medium is Diffuse Optical Tomography (DOT). In particular, such devices are intended for the in vivo localization of inhomogeneities in breast tissue of a part of a breast of a female human body. A malignant tumor is an example for such an inhomogeneity. The devices are intended to detect such inhomogeneities when they are still small, so that for example carcinoma can be detected at an early stage. A particular advantage of such devices is that the patient does not have to be exposed to the risks of examination by means of ionizing radiation, as e.g. X-rays.

WO 00/56206 A1 discloses a device for imaging the interior of a turbid medium by using a light source to irradiate the turbid medium and photodetectors for measuring a part of the light transported through the turbid medium. A control unit is provided for reconstructing an image of the interior of the turbid medium on the basis of the measured intensities. The disclosed device is particularly adapted for examining female breasts. In order to allow the examination of the turbid medium, the device is provided with a receptacle as a receiving portion enclosing a measuring volume and arranged to receive the turbid medium. Due to different sizes of the turbid media to be examined, the size of the receptacle for receiving the turbid medium does not perfectly match the size of the turbid medium, i.e. a space remains between the receptacle and the turbid medium.

The light used for examining the turbid medium has to be transmitted from the light source to the turbid medium and from the turbid medium to the photodetectors. A number of light paths coupling to the light source and a number of light paths coupling to photodetectors may be distributed across the wall bounding the measurement volume, for instance, ends of optical fibers acting as light guides are connected to the wall of the measurement volume. In a DOT measurement, the light source subsequently irradiates the turbid medium from different directions and the photodetectors measure a part of the light transmitted through the turbid medium. A plurality of such measurements are performed with the light directed to the turbid medium from different directions and, based on the results of the measurements, the control unit reconstructs the image of the examined turbid medium.

An optical matching medium for conducting optical energy generated by a light source at least from the light source to a turbid medium to be irradiated with at least a part of the optical energy generated by the light source is known from U.S. Pat. No. 5,907,406. The known optical matching medium can be used for imaging an interior of a turbid medium, such as biological tissue, using diffuse optical tomography. In medical diagnostics the matching medium may be used, for instance, for imaging an interior of a female breast. In that case, at least a part of the turbid medium, in this case a female breast, may be accommodated in the measurement volume.

In U.S. Pat. No. 5,907,406 the measurement volume is bounded by a cuplike wall portion. However, this is not always necessary. Inside the measurement volume, the part of the turbid medium under investigation is surrounded by the matching medium, so that the space inside the measurement volume not filled by the object to be imaged in general or the turbid medium in particular is filled with the matching medium. The matching medium is chosen such that the optical parameters of the matching medium, such as the absorption and scattering coefficients, are substantially identical to the corresponding optical parameters of the turbid medium. In this way, image artifacts resulting from optical boundary effects that occur when light is coupled into and out of the turbid medium can be reduced. Furthermore, use of the matching medium prevents the occurrence of an optical short-circuit in the receiving volume around the turbid medium. An optical short-circuit occurs when light is detected that has propagated along a path inside the receiving volume but outside the turbid medium and, as a consequence, has not been sufficiently scattered and attenuated. In that case the intensity of the insufficiently scattered and attenuated detected light may dwarf the intensity of detected light that has been scattered and attenuated through passage through the turbid medium.

For certain types of imaging processes, for instance, certain types of imaging an interior of a female breast, the object to be imaged is compressed between two surfaces. The question then is how to combine compression of the object to be imaged with the use of a matching medium. Several approaches have been proposed, see, for instance, *Time-Domain Optical Mammography SoftScan: Initial Results*, X. Intes, Acad. Radiol. 2005, 12:934-947 and *Diffuse Optical Tomography of Breast Cancer during Neoadjuvant Chemotherapy: A Case Study with Comparison to MRI*, R. Choe et al. MedPhys 32 (4) 2005, 1128-1139.

The latter approach has the drawback that it uses a movable plate that is submerged in the matching medium. This limits the light sources that can be used because they are sub much too. It also requires large amounts of matching medium.

SUMMARY OF THE INVENTION

It is an object of the invention to provide a detection chamber allowing compression of an object to be imaged while using a matching medium.

According to the invention this object is realized with a device according to claim 1. The invention is based on the recognition that a wall structure part of which is movable while the overall wall structure remains fluid-tight allows to define a measurement volume of variable size capable of holding an amount of fluid, such as a fluidic matching medium. With such a detection chamber, there is no need to place a light source or a detector in contact with a matching medium. They can, for instance, be optically coupled to the measurement volume using light guides or be placed behind optical windows into the measurement volume.

An embodiment of a detection chamber according to the invention is characterized in that at least part of the wall structure is transparent to light from the light source. This embodiment has the advantage that a transparent part of the wall, for instance a window, allows easy coupling of light from the light source into the measurement volume.

A further embodiment of a detection chamber according to the invention is characterized in that at least part of the wall structure is transparent to light emanating from the measurement volume. This embodiment has the advantage that a transparent part of the wall, for instance a window, allows easy coupling of light emanating from the measurement volume to a photo detector unit.

A further embodiment of a detection chamber according to the invention is characterized in that the detection chamber further comprises an overflow area for taking up a fluid from the measurement volume during reduction of the size of the measurement volume. This embodiment has the advantage that fluid that has pushed out of the measurement volume during a reduction of the volume of the measurement volume does not uncontrollably spill from the detection chamber, but is retained in the overflow area.

A further embodiment of a detection chamber according to the invention is characterized in that the detection chamber further comprises an outlet for removing a fluid from the measurement volume after imaging an object to be imaged. This embodiment has the advantage that it allows easy removal from a fluid from the measurement volume after measuring an object to be imaged.

A further embodiment of the detection chamber according to the invention is characterized in that the movable wall portion is movable by hand. Manually moving the movable wall portion has the advantage that the operator is in direct control of adjusting the size of the measurement volume. This is advantageous, for instance from a standpoint of patient safety, when the object to be imaged is a female breast to be compressed in the detection chamber. Manually moving the movable wall portion can be achieved, for instance, by manual operation of a crank handle possibly connected to a gearbox to move the movable wall portion.

The invention further relates to a device for imaging an object comprising a detection chamber according to the invention. Such a device would benefit from any one of the previous embodiment.

DETAILED DESCRIPTION OF EMBODIMENTS

Figure 1:
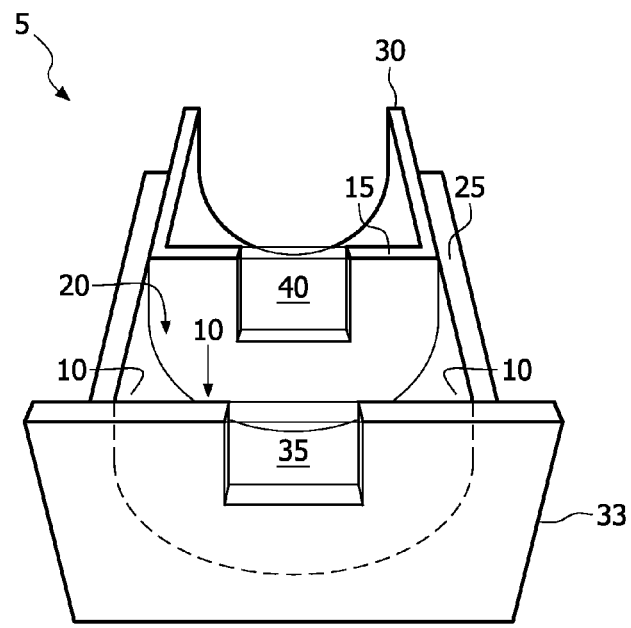
FIG. 1 schematically shows a detection chamber according to the invention.

FIG. 1 schematically shows a detection chamber according to the invention. The detection chamber (5) comprises a wall structure (10). The wall structure (10) comprises a movable wall portion (15) that can be moved as to vary the size of the measurement volume (20). The movable wall portion (15) is slidably movable in a direction perpendicular to the surface comprising window (40), see also line (63) in FIGS. 2 and 3. The overall wall structure (10) is sealed so that the wall structure (10) is fluid-tight. Consequently and by way of example, a fluid matching medium used to fill the space inside the measurement volume (20) not filled during a measurement by the object to be imaged cannot leak from the measurement volume (20). In this particular embodiment the wall structure (10, 15) is formed by two cylinders (25, 30) one of which (30) is movable inside the other (25). However, the cylindrical shape is not essential. Cylinder (25) is open along its longitudinal axis as to allow an object to be imaged access to the measurement volume (20) defined as the space between both cylinders (25, 30). The substantially cylindrical shape of cylinder (25) is indicated by the dashed semicircle on the rectangular front plate (33). Also in this particular embodiment, the wall structure (10) comprises windows (35, 40) for coupling light from a light source (not shown in the figure) into the measurement volume (20) and light emanating from the measurement volume (in response to coupling light from the light source into the measurement volume (20)) out of the measurement volume (20).

Figure 2:
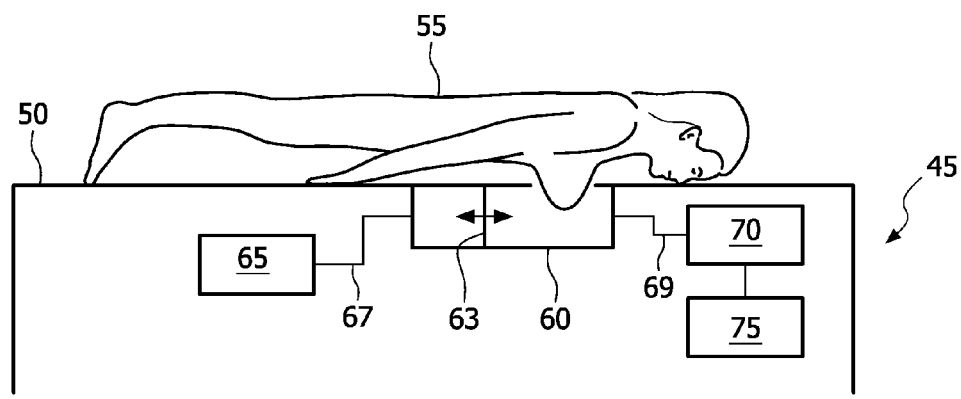
FIG. 2 schematically shows an imaging device comprising a detection chamber according to the invention.

FIG. 2 schematically shows an imaging device comprising a detection chamber according to the invention. The imaging device (45) comprises a bed-like support structure (50) for supporting a patient (55). The patient (55) lies on the support structure (50) in a chest down position. Through an opening in the support structure (50) a patient's breast hangs into the detection chamber (60) according to the invention. An embodiment of such a detection chamber (60) has been discussed in more detailed in relation to the previous figure. Line (63) with the double headed arrow indicates the movable wall portion in the detection chamber (60) according to the invention and its directions of motion. Light from a light source (65) is coupled into the measurement volume (20) comprising the patient's breast, for instance by placing the light source (65) behind one of the windows (35, 40) in FIG. 1 or by coupling the light source (65) to the measurement volume (20) using a light guide (67). Light emanating from the measurement volume (20) is coupled out of the measurement volume (20) (again, for instance, through one of the windows (35, 40) or by using light guide (69) and detected that a photo detector unit (70). Subsequently, the output of the photo detector unit is used to reconstruct an image of an interior of the object to be imaged, in this case a female breast, using image reconstruction unit (75).

Figure 3:
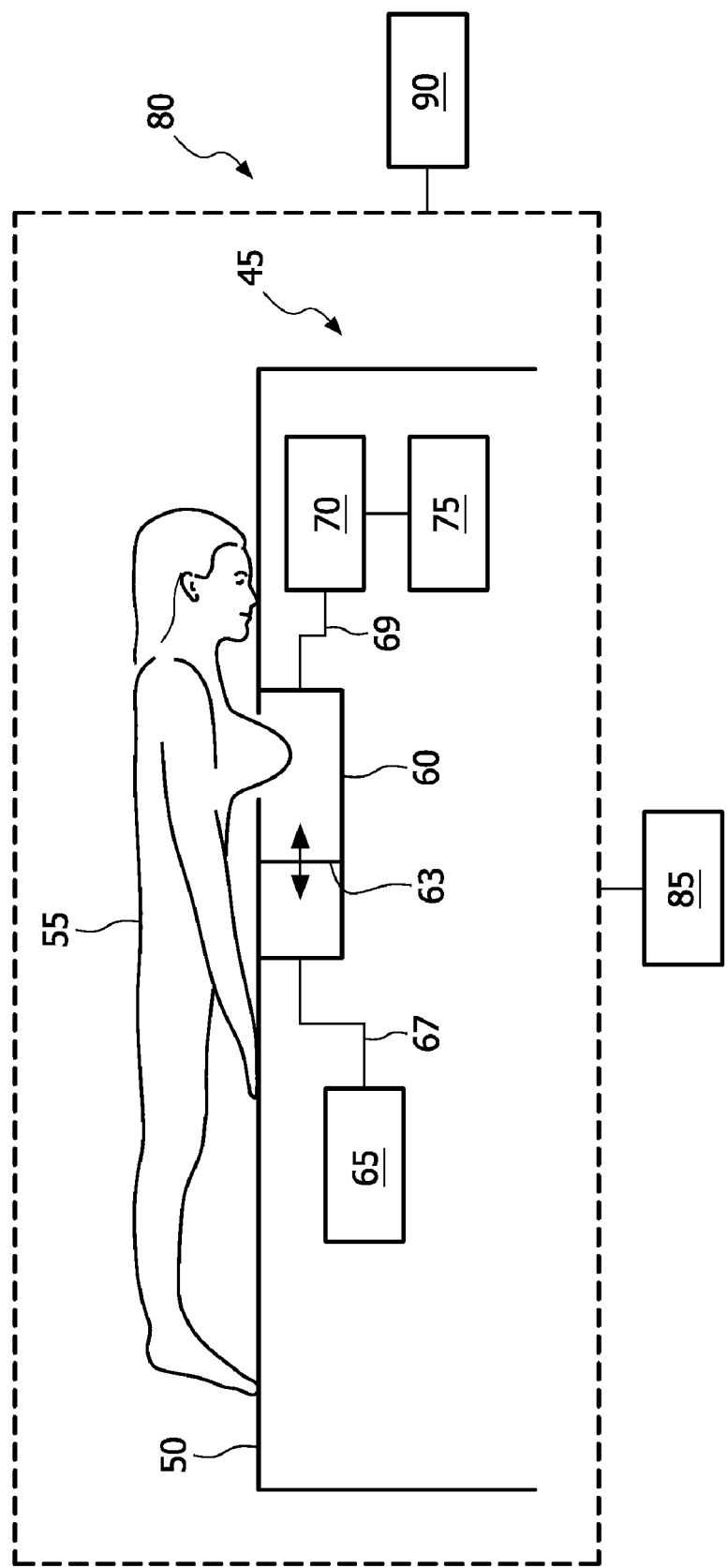
FIG. 3 schematically shows a medical imaging device comprising a detection chamber according to the invention.

FIG. 3 schematically shows a medical imaging device comprising a detection chamber according to the invention. The medical imaging device (80) comprises the imaging device (45) as discussed in relation to FIG. 2. In FIG. 3 the imaging device (45) is shown together with a patient (55). The medical imaging device (80) further comprises an operator interface (85), for instance, a keyboard allowing an operator interface with the medical imaging device (80) as well as a display (90) for displaying an image of the object to be imaged. This image may be an image of an interior of a turbid medium, for instance, a female breast reconstructed using reconstruction unit (75) and output from for the detector unit (70).

The invention claimed is:

1. A detection chamber for diagnostic imaging an object, the detection chamber comprising:
    a wall structure defining a measurement volume for holding a fluid and receiving the object to be imaged, the wall structure being arranged to couple light from a light source into the measurement volume and light emanating from the measurement volume out of the measurement volume;
    an opening in the wall structure for accommodating the object to be imaged in the measurement volume;
    a movable wall portion, comprised in the wall structure, the movable wall portion being movable as to vary the volume of the measurement volume bounded by the wall structure, wherein the wall structure comprising the movable wall portion is fluid-tight.

2. The detection chamber as claimed in claim 1, wherein at least part of the wall structure is transparent to light from the light source.

3. The detection chamber as claimed in claim 1, wherein at least part of the wall structure is transparent to light emanating from the measurement volume.

4. The detection chamber as claimed in claim 1, wherein the detection chamber further comprises an outlet for venting the fluid from the measurement volume after imaging the object to be imaged.

5. The detection chamber as claimed in claim 1, wherein the movable wall portion is movable by hand.

6. A device for imaging an object comprising the detection chamber as claimed in claim 1.

7. The device for imaging an object as claimed in claim 6, wherein the device is a medical imaging device.

8. A detection chamber for diagnostic imaging an object, the detection chamber comprising:
    a wall structure defining a measurement volume for receiving the object to be imaged, the wall structure being arranged to couple light from a light source into the measurement volume and light emanating from the measurement volume out of the measurement volume;
    an opening in the wall structure for accommodating the object to be imaged in the measurement volume;
    a movable wall portion, comprised in the wall structure, the movable wall portion being movable as to vary a size of the measurement volume bounded by the wall structure, wherein the wall structure comprising the movable wall portion is fluid-tight; and
    an overflow area for taking up a fluid from the measurement volume during reduction of the size of the measurement volume.

9. The detection chamber as claimed in claim 8, wherein at least part of the wall structure is transparent to light from the light source.

10. The detection chamber as claimed in claim 8, wherein at least part of the wall structure is transparent to light emanating from the measurement volume.

11. The detection chamber as claimed in claim 8, wherein the detection chamber further comprises an outlet for venting the fluid from the measurement volume after imaging the object to be imaged.

12. The detection chamber as claimed in claim 8, wherein the movable wall portion is movable by hand.

13. A device for imaging an object comprising the detection chamber as claimed in claim 8.

14. The device for imaging an object as claimed in claim 13, wherein the device comprises a medical imaging device.

15. A detection chamber for diagnostic imaging an object, the detection chamber comprising:
    a fluid-tight wall structure comprising a movable wall portion defining a measurement volume for holding a fluid and receiving the object to be imaged within the fluid, the wall structure being configured to couple light from a light source to the measurement volume and from the measurement volume to a photo detector unit,
    wherein the movable wall portion is operable to vary a size of the measurement volume within the wall structure.

16. The detection chamber as claimed in claim 15, wherein at least part of the wall structure is transparent to light from the light source and at least part of the wall structure is transparent to light emanating from the measurement volume.

17. The detection chamber as claimed in claim 15, wherein the movable wall portion is movable by hand.

18. The detection chamber as claimed in claim 15, wherein the wall structure comprises a first cylinder and the movable wall portion comprises a second cylinder movable within the first cylinder.

* * * * *